US00PP29046P3

(12) United States Plant Patent
Hooijman

(10) Patent No.: US PP29,046 P3
(45) Date of Patent: Mar. 6, 2018

(54) ROSE PLANT NAMED 'ESM R197'

(50) Latin Name: *Rosa hybrida*
Varietal Denomination: ESM R197

(71) Applicant: ESMERALDA BREEDING B.V., Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 85 days.

(21) Appl. No.: 14/998,737

(22) Filed: Feb. 9, 2016

(65) Prior Publication Data

US 2017/0231131 P1 Aug. 10, 2017

(51) Int. Cl.
*A01H 5/02* (2006.01)

(52) U.S. Cl.
USPC ..... Plt./151

(58) Field of Classification Search
USPC ..... Plt./151
See application file for complete search history.

(56) References Cited

PUBLICATIONS

UPOV hit on Rose plant named 'ESM R197', KE PBR ROS 16 1458, Jan. 13, 2016.*
UPOV hit on Rose plant named 'ESM R197', QZ PBR 43824, Oct. 15, 2014.*

* cited by examiner

*Primary Examiner* — Anne M Grunberg
(74) *Attorney, Agent, or Firm* — C. A. Whealy

(57) ABSTRACT

A new and distinct cultivar of Rose plant named 'ESM R197', characterized by its upright and strong flowering stems; moderately vigorous to vigorous growth habit; dark green-colored leaves; relatively tall flower buds; red-colored flowers; good productivity with about one flowering stem developing per plant each month; and excellent postproduction longevity.

1 Drawing Sheet

Botanical designation: *Rosa hybrida.*
Cultivar denomination: 'ESM R197'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R197'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in July, 2010 of a proprietary Rose selection identified as Line 28, not patented, as the female, or seed, parent with a proprietary Rose selection identified as Line 406, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in September, 2011.

Asexual reproduction of the new Rose plant by bud grafting in El Quinche, Pichincha, Ecuador since October, 2011 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R197'. These characteristics in combination distinguish 'ESM R197' as a new and distinct Rose plant:

1. Upright and strong flowering stems.
2. Moderately vigorous to vigorous growth habit.
3. Dark green-colored leaves.
4. Relatively tall flower buds.
5. Red-colored flowers.
6. Good productivity with about one flowering stem developing per plant each month.
7. Excellent postproduction longevity.

Plants of the new Rose differ from plants of the female parent selection in the following characteristics:

1. Plants of the new Rose have taller flower buds than plants of the female parent selection.
2. Flowers of plants of the new Rose have more than twice as many petals as flowers of plants of the female parent selection.
3. Cut flowering stems of plants of the new Rose last about four days longer than cut flowering stems of plants of the female parent selection.
4. Plants of the new Rose and the female parent selection differ in flower color as plants of the female parent selection have pink-colored flowers.

Plants of the new Rose differ from plants of the male parent selection in the following characteristics:

1. Plants of the new Rose are slightly less vigorous as plants of the male parent selection.
2. Plants of the new Rose have taller flower buds than plants of the male parent selection.
3. Cut flowering stems of plants of the new Rose last about six days longer than cut flowering stems of plants of the male parent selection.

Plants of the new Rose can be compared to plants of *Rosa hybrida* 'Freedom', not patented. In side-by-side comparisons conducted in El Quinche, Pichincha, Ecuador, plants of the new Rose differed from plants of 'Freedom' in the following characteristics:

1. Plants of the new Rose were slightly more vigorous than plants of 'Freedom'.
2. Plants of the new Rose were more freely branching and produced more flowering stems per year than plants of 'Freedom'.
3. Plants of the new Rose had taller flower buds than plants of 'Freedom'.
4. Flowers of plants of the new Rose opened about seven to nine days quicker than flowers of plants of 'Freedom'.
5. Plants of the new Rose had larger flowers than plants of 'Freedom'.
6. Cut flowers of plants of the new Rose lasted about eight to ten days longer than cut flowers of plants of 'Freedom'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the left of the sheet is a side perspective of a typical flowering stem of 'ESM R197'.

The photograph at the upper right of the sheet is a close-up view of a typical developed flower of 'ESM R197'.

The photographs at the lower right of the sheet are close-up views of the upper and lower surfaces of typical leaves of 'ESM R197'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched 13 to 14 weeks after planting and were 46 weeks old when the photographs were taken and 89 weeks old when the description was taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R197'.

Parentage:

*Female, or seed, parent.*—Proprietary seedling selection of *Rosa hybrida* identified Line 28, not patented.

*Male, or pollen, parent.*—Proprietary seedling selection of *Rosa hybrida* identified Line 406, not patented.

Propagation:

*Type.*—By bud grafting.

*Time to initiate roots, summer.*—About 15 days at temperatures about 26° C. to 30° C.

*Time to produce a rooted young plant, summer.*—About 30 days at temperatures about 22° C. to 26° C.

*Root description.*—Medium in thickness, fibrous; close to N199B in color.

*Rooting habit.*—Moderately freely branching; medium density.

Plant description:

*Plant and growth habit.*—Perennial shrub; upright and strong flowering stems; typically grown as a standard type; moderately vigorous to vigorous growth habit.

*Productivity.*—Plants of the new Rose are highly productive with about 13.08 flowering stems developing per plant per year.

*Plant height.*—About 136 cm.

*Plant width (spread).*—About 63 cm.

*Lateral branches.*—Quantity: Freely branching habit with about 18 lateral branches developing per plant. Length: About 128 cm. Diameter: About 7.4 mm. Internode length: About 5.6 cm. Texture: Smooth, glabrous; older stems, woody. Strength: Moderately strong to strong. Color: Close to 146B and N199C. Thorns: Density: Moderate to abundant. Shape: Triangular with sharp acuminate apices; slightly incurved. Height: About 8.7 mm. Length, at base: About 8.9 mm. Color, immature: Close to 187C. Color, mature: Close to 185A.

Leaf description:

*Arrangement.*—Alternate; compound with typically seven leaflets per leaf.

*Leaf length.*—About 16.7 cm.

*Leaf width.*—About 10.2 cm.

*Terminal leaflet length.*—About 5.7 cm.

*Terminal leaflet width.*—About 3.4 cm.

*Lateral leaflet length.*—About 4.9 cm.

*Lateral leaflet width.*—About 3 cm.

*Leaflet shape.*—Ovate.

*Leaflet apex.*—Acute.

*Leaflet base.*—Short attenuate.

*Leaflet margin.*—Serrate.

*Leaflet texture, upper and lower surfaces.*—Smooth, glabrous; papery to coriaceous.

*Leaflet venation pattern.*—Pinnate.

*Leaflet color.*—Developing leaflets, upper surface: Close to N77A and 147A. Developing leaflets, lower surface: Close to N199A and 59A. Fully expanded leaflets, upper surface: Close to 139A; venation, close to 146A and N77A. Fully expanded leaflets, lower surface: Close to 147B; venation, close to 146B.

*Petioles, leaves.*—Length: About 1.4 cm. Diameter: About 1.9 mm. Texture, upper surface: Prickly. Texture, lower surface: Smooth, glabrous. Color, upper surface: Close to 166A and 199A. Color, lower surface: Close to 146B.

*Petioles, leaflets.*—Length: About 2.2 cm. Diameter: About 1.4 mm. Texture, upper surface: Prickly. Texture, lower surface: Smooth, glabrous. Color, upper surface: Close to 166A and 199A. Color, lower surface: Close to 148D.

*Stipules.*—Arrangement and appearance: Two, adnate to the petiole, leafy in appearance. Length: About 3.4 cm. Width: About 3.2 mm. Shape: Roughly deltoid. Apex: Acuminate, tapered. Base: Tapered. Margin: Entire. Texture, upper and lower surfaces: Smooth; membranous. Venation pattern: Pinnate. Color, upper surface: Close to 137B. Color, lower surface: Close to 146A.

Flower description:

*Flower type and arrangement.*—Symmetrical rosette flowers; flowers typically grown as a standard type with one terminal flower per flowering stem; flowers face upright.

*Flowering season.*—Plants of the new Rose flower year-round under greenhouse conditions; early flowering habit, plants begin flowering about 78 days after pinching.

*Flower diameter.*—About 12.5 cm.

*Flower depth (height).*—About 5.8 cm.

*Flower longevity.*—Excellent postproduction longevity; flowers maintain good substance for about 20 to 22 days on the plant and for about 16 to 18 days as a cut flower; flowers persistent.

*Fragrance.*—Slightly fragrant.

*Flower buds.*—Rate of opening: About 18 to 20 days. Length: About 6.6 cm. Diameter: About 5.5 cm. Shape: Ovoid. Color: Close to 146B and 199A.

*Petals.*—Quantity: About 50 per flower; petals imbricate. Length: About 6 cm. Width: About 6.15 cm. Shape: Nearly round; transversely ovate. Apex: Blunt to short acute. Base: Obtuse. Margin: Entire. Texture, upper and lower surfaces: Smooth, glabrous; papery to coriaceous. Color: When opening, upper surface: Close to 53A; towards the base, close to 145C. When opening, lower surface: Close to 60A; towards the base, close to 145C. Fully opened, upper surface: Close to 46A; towards the base, close to 1C. Fully opened, lower surface: Close to 53B; towards the base, close to 154D.

*Petaloids.*—Quantity: About five; whorled. Length: Variable. Width: Variable. Shape: Irregularly shaped. Apex: Blunt to short acute. Base: Obtuse. Margin: Mostly uneven. Texture, upper and lower surfaces: Smooth, glabrous; papery to coriaceous. Color: When opening, upper and lower surfaces: Close to 53A and 155A. Fully opened, upper and lower surfaces: Close to 53A and 155C.

*Sepals.*—Quantity per flower: Typically five in a single whorl. Length: About 5.18 cm. Width: About 1.24 cm. Shape: Roughly deltoid. Apex: Tapered. Base: Truncate. Margin: Entire; ciliate and/or glandular. Texture, upper and lower surfaces: Leathery. Color: When opening, upper surface: Close to 146A to 146D. When opening, lower surface: Close to 146B and 145A. Fully opened, upper surface: Close to 146A and 145B. Fully opened, lower surface: Close to 146A and 145A.

*Reproductive organs.*—Stamens: Quantity: About 223 per flower. Anther length; About 3.2 mm. Anther shape: Reniform. Anther color: Close to 21B and 20D. Filament color: Close to 160A and 184C. Pollen amount: Abundant. Pollen color: Close to 167B. Pistils: Quantity: About 265 per flower. Pistil length: About 1.5 cm. Stigma shape: Broadly reniform. Stigma color: Close to 160A. Style length: About 1 cm. Style color: Close to 39C and 160D. Receptacle height: About 1.2 cm. Receptacle diameter: About 1.33 cm. Receptacle shape: Cup-shaped. Receptacle texture: Smooth, glabrous. Receptacle color: Close to 144A. Fruits: Length: About 2.8 cm. Diameter: About 2.3 cm. Texture: Slightly rough. Color: Close to 167A and N144A. Seeds: Quantity per fruit: About 16. Length: About 7.9 mm. Diameter: About 4.4 mm. Texture: Smooth. Color: Close to 151B and 160C.

Pathogen & pest tolerance: Plants of the new Rose have been observed to have moderate tolerance to Powdery Mildew, Downy Mildew and *Botrytis*. Plants of the new Rose have not been observed to be tolerant to pests and other pathogens common to Rose plants.

Temperature tolerance: Plants of the new Rose have been observed to tolerate temperatures ranging from 0° C. to 35° C.

It is claimed:

1. A new and distinct Rose plant named 'ESM R197' as illustrated and described.

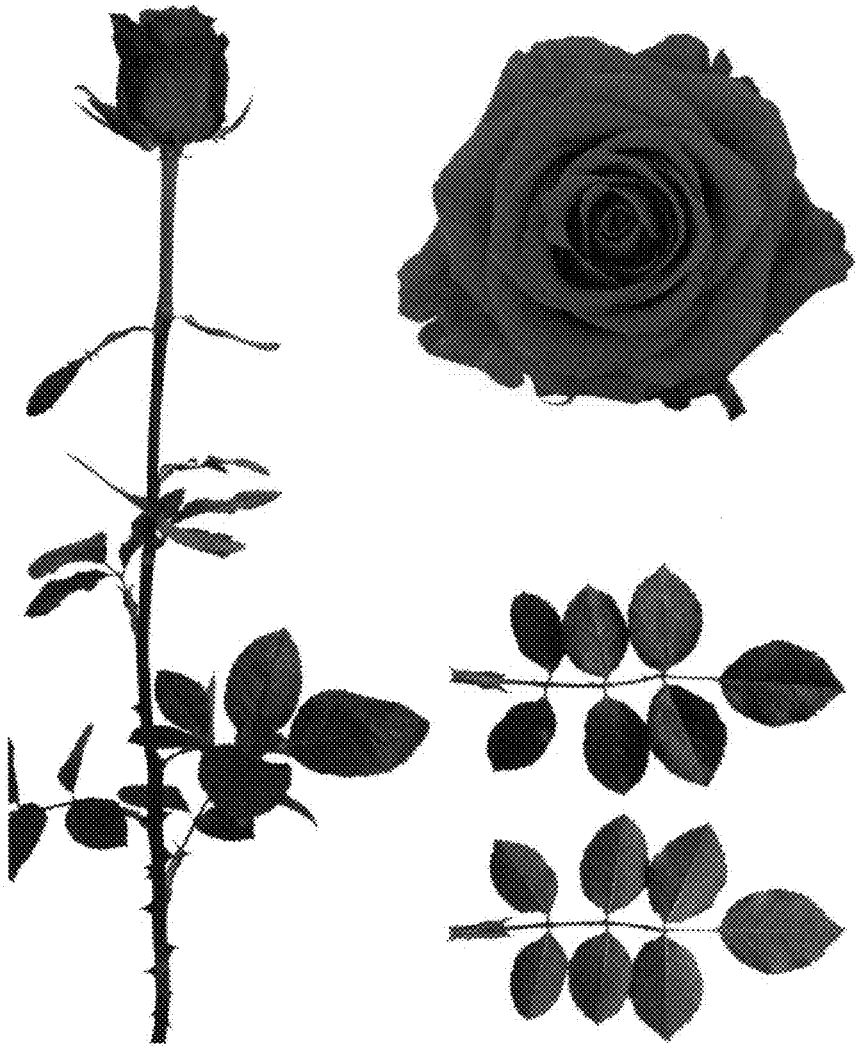

* * * * *